United States Patent [19]

Stackebrandt et al.

[11] Patent Number: 5,582,993
[45] Date of Patent: Dec. 10, 1996

[54] COMPOSITIONS AND METHODS FOR THE DETECTION OF BACTERIA IN THE GENUS VIBRIO

[75] Inventors: Erko Stackebrandt, Bardon, Australia; David J. Lane, Milford, Mass.

[73] Assignee: Amoco Corporation, Chicago, Ill.

[21] Appl. No.: 402,964

[22] Filed: Mar. 10, 1995

Related U.S. Application Data

[63] Continuation of Ser. No. 138,862, Oct. 19, 1993, abandoned, which is a continuation of Ser. No. 700,785, May 15, 1991, abandoned.

[51] Int. Cl.$^6$ .............. C12Q 1/68; C12P 19/34; C07H 21/04; C12N 15/00
[52] U.S. Cl. .............. 435/6; 435/91.1; 435/909; 435/91.32; 536/23.1; 536/24.3; 536/24.32; 935/8; 935/78
[58] Field of Search .............. 435/6, 91.1, 909, 435/91.32; 536/23.1, 24.3, 24.32; 935/8, 78

[56] References Cited

U.S. PATENT DOCUMENTS

| | | | |
|---|---|---|---|
| 5,049,489 | 9/1991 | Aldrich et al. | 435/6 |
| 5,087,558 | 2/1992 | Webster, Jr. | 435/5 |
| 5,258,284 | 11/1993 | Morris, Jr. et al. | 435/6 |

FOREIGN PATENT DOCUMENTS 8803957  2/1988  WIPO.

OTHER PUBLICATIONS

Chuba et al. J. of Gen. Microb. 134:1931–(1988).
Worse Microbiol. Reviews. 51(2):221 (1987).
Chen et al. FEMS Microb. Lett 57:19–24 (1989).
Borosius et al. P.N.A.S. 75(10):4801 (1978).
Lane et al., PNAS, USA, 82(20):6955–6959, Oct. 1989.
Rehnstam et al., Appenv Microb 55(8): 1907–10, Aug. 1989.
Molitoris et al., Int. J Sys Bact 39(4):442–449, Oct. 1989.
Nishibuchi et al., Int Immun 49(3): 481–486, Sep. 1985.
Morris, Jr., et al., Appl Envir Mcrb 53(1):193–195, Jan. 1987.
Rehnstam et al. Appl. Env. Microb. 55(8):1907 (1989).
Valle O. et al. Syst. appl. Microb.(ABS) 13:257 (1990).

Primary Examiner—Stephanie W. Zitomer
Assistant Examiner—Bradley L. Sisson
Attorney, Agent, or Firm—Norval B. Galloway

[57] ABSTRACT

The nucleic acid compositions and methods are presented which are capable of preferentially hybridizing to rRNA or rDNA of Vibrio bacteria over rRNA or rDNA of non-Vibrio bacteria having utility assay means for detection.

26 Claims, 1 Drawing Sheet

COMPOSITIONS AND METHODS FOR THE DETECTION OF BACTERIA IN THE GENUS VIBRIO

This is a continuation of application Ser. No. 08/138,862, filed Oct. 19, 1993, now abandoned, which is a continuation of Ser. No. 07/700,785, filed May 15, 1991, now abandoned.

FIELD OF THE INVENTION

This invention relates to compositions and methods for detecting bacteria belonging to the genus Vibrio.

BACKGROUND OF THE INVENTION

The following definitions are provided to facilitate an understanding of the present invention.

The term "Vibrio" as used herein, refers to the bacteria classified as such in Bergey's Manual of Systematic Bacteriology (N. R. Krieg [ed.], 1984, 516–538, Williams & Wilkins). Detection of Vibrio is important in various medical and public health contexts. The Vibrio are important agents of human disease. Vibrio bacteria can cause a variety of pathological conditions ranging from simple gastroenteritis to more severe illnesses.

The term "target" or "target molecule," in a diagnostic sense, refers to a molecule of interest, i.e. the molecule whose presence one wishes to Know. In a therapeutic sense, the term "target" or "target molecule" refers to a molecule associated with a disease or with an organism causing a disease.

The term "biological binding pair" as used in the present application refers to any pair of molecules which exhibit mutual affinity or binding capacity. A biological binding pair is capable of forming a complex under binding conditions. For the purposes of the present application, the term "ligand" will refer to one molecule of the biological binding pair, and the term "antiligand" or "receptor" will refer to the opposite molecule of the biological binding pair. For example, without limitation, embodiments of the present invention have application in nucleic acid hybridization assays where the biological binding pair includes two complementary nucleic acids. One of the nucleic acids is designated the ligand and the other nucleic acid is designated the antiligand or receptor. One of the nucleic acids may also be a target molecule. The designation of ligand or antiligand is a matter of arbitrary convenience. The biological binding pair may include antigens and antibodies, drugs and drug receptor sites, and enzymes and enzyme substrates, to name a few.

The term "probe" refers to a ligand of known qualities capable of selectively binding to a target antiligand or receptor. As applied to nucleic acids, the term "probe" refers to nucleic acid having a base sequence complementary to a target nucleic acid. The probe and the target are capable of forming a probe target complex under binding conditions. The term "probe" will be used herein, in both a diagnostic sense, meaning capable of binding a molecule, the presence or absence of which one desires to know, and a therapeutic sense, capable of binding to a molecule associated with a disease.

The term "label" refers to a chemical moiety which is capable of detection including, by way of example, without limitation, radioactive isotopes, enzymes, luminescent agents, precipitating agents, and dyes. The term "agent" is used in a broad sense, including any chemical moiety which participates in reactions which lead to a detectable response. The term "cofactor" is used broadly to include any chemical moiety which participates in reactions with the label.

The term "amplify" is used in the broad sense to mean creating an amplification product, which may include by way of example, additional target molecules, or target-like molecules, capable of functioning in a manner like the target molecule, or a molecule subject to detection steps in place of the target molecule, which molecules are created by virtue of the presence of the target molecule in the sample. In the situation where the target is a polynucleotide, additional target, or target-like molecules, or molecules subject to detection can be made enzymatically with DNA or RNA polymerase.

The term "contiguous" means an adjacent area of a molecule. By way of example, in the case of biological binding pairs, where a first ligand binds to a receptor target molecule, the area surrounding and adjacent to the first ligand is open and capable of binding to a second ligand contiguous to the first. In the context of nucleic acid, where a first probe binds to an area of a larger nucleic acid target molecule, an adjacent mutually exclusive area along the length of the target molecule can bind to a second probe which will then be contiguous to the first. The target molecule acts as a template, directing the position of the first probe and the second probe. The term "substantially contiguous" is used in the functional sense to include spatial orientations which may not touch, may not abut, or may overlap, yet function to bring parts, areas, segments and the like into cooperating relationship.

The term "capture ligand" means a ligand capable of specifically binding with a capture antiligand associated with a support.

The term "support" when used alone, includes conventional supports such as filters, dipsticks and membranes as well as retrievable supports.

Genetic information is stored in living cells in thread-like molecules of DNA. In vivo, the DNA molecule is a double helix of two complementary strands of DNA, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding and π-stacking interactions. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand. The genetic code of a living organism is carried upon the DNA strand, in the sequence of base pairs.

Molecules of DNA consist of covalently linked chains of deoxyribonucleotides and molecules of RNA consists of covalently linked chains of ribonucleotides. Each nucleic acid is linked by a phosphodiester bridge between the 5'-hydroxyl group of the sugar of one nucleotide and the 3'-hydroxyl group of the sugar of an adjacent nucleotide. The terminal ends of nucleic acid are often referred to as being 5'-termini or 3'-termini in reference to the terminal functional group. Complementary strands of DNA and RNA form antiparallel complexes in which the 3'-terminal end of one strand is oriented and bound to the 5'-terminal end of the opposing strand.

Nucleic acid hybridization assays are based on the characteristic of two nucleic acid strands to pair at their complementary regions to form hybrids. The formation of such hybrids can be made to be highly specific by adjustment of the conditions (sometimes referred to as stringency) under which this hybridization takes place such that hybridization will not occur unless the sequences are precisely complementary. If total nucleic acid from the sample is immobilized on a solid support such as a nitrocellulose membrane, the presence of a specific "target" sequence in the sample can be determined by the binding of a complementary nucleic acid "probe" which bears a label. After removal of non-hybridized probe by washing the support, the amount of target is determined by the amount of detectable moiety present.

Nucleic acid probes by design or selection, contain specific nucleotide sequences that allow them to hybridize under hybridization conditions, specifically and preferentially, to target nucleic acid sequences. The term "preferentially" is used in a relative sense, one hybridization reaction product is more stable than another under identical conditions. Under some conditions, a hybridization reaction product may be formed with respect to one target, but not to another potential binding partner.

Although, nucleic acid compositions of great length, up to 2500 nucleotides, have been suggested for use as probes, there are practical considerations which would suggest a smaller nucleic acid would have some advantage. A minimum of ten nucleotides are necessary in order to statistically obtain specificity and form stable hybridization products. A maximum of 250 nucleotides represents an approximate upper limit of sequences in which reaction parameters can be readily adjusted and controlled presently to determine mismatched sequences and preferential hybridization. The maximum 250 nucleotides also represent the upper limit of most DNA and RNA synthesis equipment. Most preferably, probe sequences have between 20 to 60 nucleotides.

Hybridization conditions are defined by the base composition of the probe/target duplex, as well as by the level and geometry of mispairing between the two nucleic acids. Normal hybridization conditions for nucleic acid of 10 to 250 bases are a temperature of approximately 60° C. in the presence of 1.08M sodium chloride, 60 mM sodium phosphate, and 6 mM ethylenediamine tetraacetic acid (pH of 7.4).

Reaction parameters which are commonly adjusted include concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which hybridization is to take place (e.g., based on the type of assay to be performed) will dictate certain characteristics of the preferred probes to be employed. Such relationships are well understood and can be readily manipulated by those skilled in the art.

Ribosomes are of profound importance to all organisms. Ribosomes serve as the only known means of translating genetic information into cellular proteins, the math structural and catalytic elements of life. A clear manifestation of this importance is the observation that all cells have ribosomes.

Bacterial ribosomes contain three distinct RNA molecules which, at least in *Escherichia coli*, re referred to as 5S, 16S and 23S rRNAs. In eukaryotic organisms, there re four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 16S, and 23S rRNA generic names for the homologous RNA molecules in any bacterium and this convention will be continued herein. Detailed discussion of the 16S and 23S rRNA primary and secondary structures my be found in Gutell, ei.al. (Progress in Nucleic Acid Research, vol. 32, 1985) and Gutell and Fox (Nucleic Acids Research, vol. 16 supplement, 1988).

Kohne et al. (1968) Biophysical Journal 18:1104–1118 discuss one method for preparing probes to rRNA sequences.

Pace and Campbell, Journal of Bacteriology 107:543–547 (1971), discuss the homology of ribosomal ribonucleic acids from diverse bacterial species and a hybridization method for quantitating such homology levels. Similarly, Sogin et al., Journal of Molecular Evolution 1:173–184 (1972), discuss the theoretical and practical aspects of using primary structural characterization of different ribosomal RNA molecules for evaluating phylogenetic relationships.

Fox et al., International Journal of Systematic Bacteriology (1977), discuss the comparative cataloging of 16S ribosomal RNAs as an approach to prokaryotic systematics.

SUMMARY OF THE INVENTION

The present invention relates to detecting bacteria belonging to he genus Vibrio. More specifically, embodiments of the present invention provide nucleic acid compositions and methods for their use for the specific detection of Vibrio bacteria.

One embodiment of the present invention features, as a composition of matter, a nucleic acid comprising 10 to 250 nucleotides capable of preferentially hybridizing to rRNA or rDNA of Vibrio bacteria over rRNA or rDNA of non-Vibrio bacteria.

Preferably, the nucleic acid is capable of preferentially hybridizing to a region of 16S rRNA or rDNA selected from the group of regions consisting of 132–154, 154–167, 446–488, 580–761, 614–626, 896–903, and 1123–1149. Compositions of the present invention are capable of hybridizing preferentially to one or more of the Vibrio bacteria, *V. alginolyticus, V. campbellii, V. protiolyticus, V. parahaemolyticus, V. hollisae, V. anhuillarum, V. diazotrophicus, V. vulnificus, V. harveyi* and *V. nartiegens*.

A further embodiment of the present invention features, as a composition of matter, a nucleic acid comprising 10 to 250 nucleotides capable of preferentially hybridizing to rRNA or rDNA of one or more Vibrio bacteria selected from the group of Vibrio bacteria consisting of *V. alginolyticus, V. campbellii, V. proteolyticus, V. parahaemolyticus, V. hollisae, V. anguillarum, V. diazotrophicus, V. vulnificus, V. harveyi and V. natriegens* over non-selected Vibrio bacteria of the same group. The nucleic acid is capable of preferentially, hybridizing to a region of the 16S rRNA or rDNA selected from the group of regions consisting of 73–100, 80–196 and 455–477.

A further embodiment of the present invention features a method for detecting Vibrio bacteria in a sample comprising the steps of contacting the sample with a nucleic acid comprising 10 to 250 nucleotides capable of preferentially hybridizing to rRNA or rDNA of Vibrio bacteria over rRNA or rDNA of non-Vibrio bacteria. Hybridization conditions are imposed on the sample and the nucleic acid is allowed to form a hybridization product in the presence of rRNA or rDNA of Vibrio bacteria. The hybridization product is detected as an indication of the presence of Vibrio bacteria.

Preferably, the nucleic acid of the present method is capable of preferentially, hybridizing to a region of the 16S rRNA or rDNA selected from the group of regions consisting of 132–154, 154–167, 446–488, 580–761, 614–626, 896–903, and 1123–1149. Embodiments of the present invention are capable of detecting the presence of *V. alginolyticus, V. campbellii, V. proteolyticus, V. parahaemolyticus, V. hollsae, V. anguillarum, V. dazotrophicus, V. vulnfcus, V. harveyi* and *V. natriegens.*

A further embodiment of the present invention features a method for detecting one or more Vibrio bacteria in a sample selected from the group of Vibrio bacteria consisting of *V. alginolyticus, V. campbellii, V. proteolyticus, V. parahaemolyticus, V. hollisae, V. anguillarum, V. diazotrophicus, V. vulnificus, V. harveyi* and *V. nartiegens* over non-selected Vibrio bacteria of the same group. The method comprises the step of contacting the sample with a nucleic acid having 10 to 250 nucleotides capable of preferentially hybridizing to rRNA or rDNA of the selected Vibrio bacteria over non-selected Vibrio bacteria of the same group. Hybridization conditions are imposed on the sample and the nucleic acid compositions to allow the formation of a hybridization product in the presence of the selected Vibrio bacteria. Detection of the hybridization product is an indication of the presence of the selected Vibrio bacteria. Preferably, the nucleic acid is capable of preferentially hybridizing to one or more regions of the 16S rRNA or rDNA selected from the group of consisting of 73–100, 180–196 and 455–477.

The compositions of the present invention can be assembled in advance to form a kit. Such a kit may be used to detect the presence of Vibrio bacteria. Such kits normally contain reagents maintained in suitable containment vessels, ancillary equipment and instructions for their use. Reagents would comprise compositions described herein.

Other aspects and advantages of the present invention will become apparent upon consideration of the following detailed description, according to presently preferred embodiments of the invention.

BRIEF DESCRIPTION OF THE FIGURES AND TABLES

Figure 1:
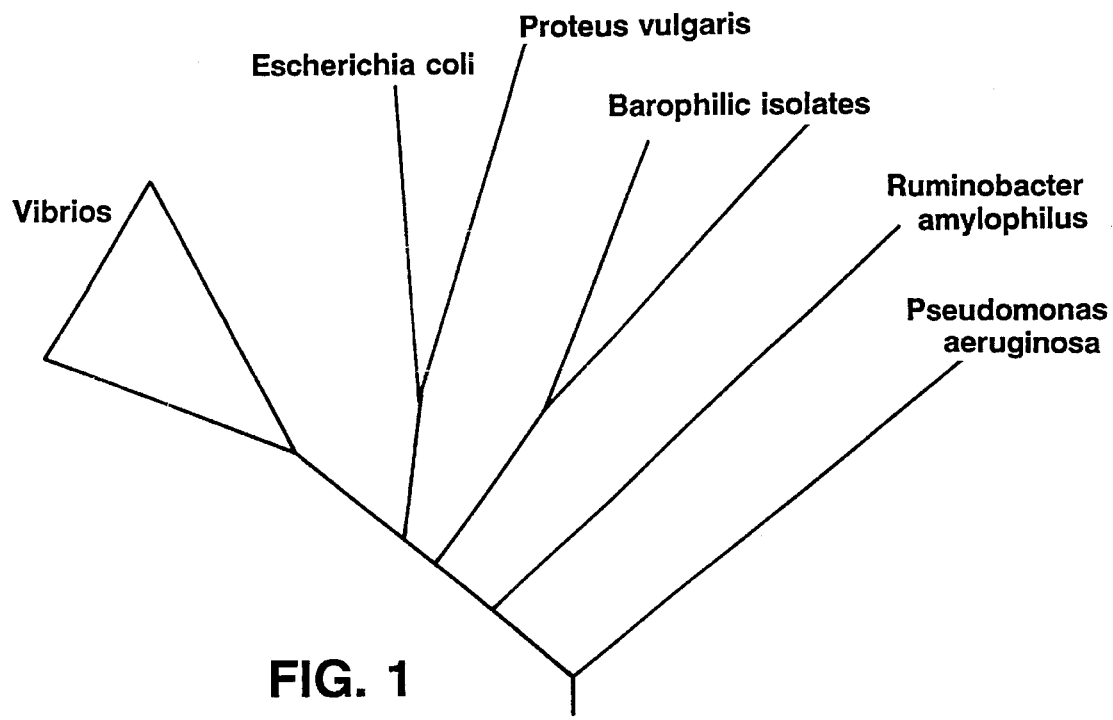
FIG. 1 is a schematic representation of the relationship of Vibrio bacteria to *Escherichia coli, Proteus vulgaris, Barophilic isolates, Ruminobacier amylophilus, Pseudomonas aeruginosa.*
Figure 2:
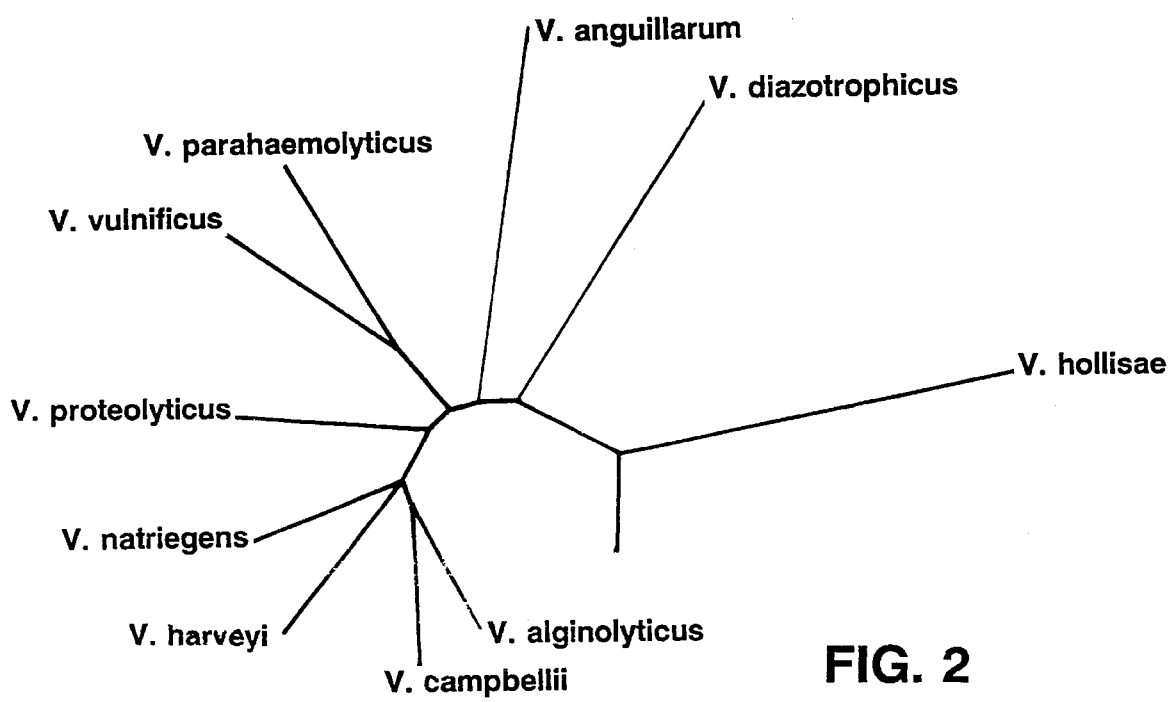
FIG. 2 is a diagram of the relationship of the various Vibrio species including *V. alginolyticus, V. ampbellii, V. hrveyi, V. nartiegens, V. proteolyticus, V. vulnificus, V. parahaemolyticus, V. anguillarum, V. diazotrophicus,* and *V. hollisae.*

Table 1 sets forth various Vibrio species, source and accession numbers utilized in the Examples below.

Table 2 sets forth equally weighted (Hamming) distances between 16S rRNA sequence pairs of Vibrio species and other members of the same name or subclass of proteo bacteria.

Table 3 sets forth sequence signature data distinguishing members of Vibrio from other gamma-3 proteo bacteria.

Table 4 sets forth variable 16S rRNA stretches that can be used as targets for oligonucleotide probing and PCR diagnostic processes.

DETAILED DESCRIPTION

The following examples illustrate the practice of the invention according to certain preferred procedures.

A. Material and Methods

Microorganisms

The strains investigated are listed in Table 1. Strains were grown at GENE-TRAK Systems Corporation, Framingham, Mass. USA, using the standard culture medium recommended in the ATCC catalog. The growth conditions are briefly set forth below:

| | |
|---|---|
| *Y. campbellii* | Marine agar, room temp, overnight |
| *V. harveyi* | Photobacterium agar, room temp, overnight |
| *V. alginolyticus* | Trypticase soy agar with 3% salt (bactobile salt [1 gram/liter] plus 3% NaCl), 37° C., overnight |
| *V. natriegens* | Nutrient agar with 1.5% NaC., room temp, overnight |
| *V. anguillarum* | Enriched nutrient agar, room temp, overnight |
| *V. diazotrophicus* | Marine agar, room temp, overnight |
| *V. proteolyticus* | Nutrient agar with 3% NaCl. room temp, overnight |
| *V. parahemolyticus* | Nutrient agar with 3% NaCl, 37° C., overnight |
| *V. vulnificus* | Marine agar, 30° C., overnight |
| *V. hollisae* | Marine agar, 30° C., overnight |

Isolation, extraction and analysis of 16S rRNA was as described (Lane, "16S/23S rRNA Sequencing," p. 115–174 in Stackebrandt et al. (eds.), Nucleic Acid Techniques in Bacterial Systems, Wiley & Sons, New York, 1991) and shipped and stored, as lyophylized powders. Isolation and sequence analysis (Lane et al. *Proc. Natl. Acad. Sci.,* 82:6955–6959, 1985; StacKebrandt and Charfreitag *J. Gen. Microbiol.* 136:37–43, 1990) followed described procedures. The sequences were aligned to the homologous regions of sequences from several reference bacteria: *Vibrio anguillarum* (Valle et al. *Syst. Appl. Microbiol.* 13:257, 1990), *E. coli, Proteus vulgaris, Ruminobacter amylophilus, Pseudomonas aeruginosa* (DeWachter et al., 1990) and two barophilic strains (accession numbers X54744 and X54745, Liesack et al. *Microb. Ecol.,* 21:191–198, 1991). The phylogenetic analysis was carried out by the neighborliness method (Fitch, *J. Mol. Evol.,* 18:30–37 1981; Sattath and Tversky *Psyohometrika,* 42:319–345, 1977) with algorithms implemented as part of the program package SAGE (Technoma, Heidelberg, F.R.G.) designed for the IBM XT/AT and compatible computers.

B. Results and Discussion

The primary structure of the 16S rRNA of the type strains of 8 Vibrio species and of *V. harveyi* ATCC 14084 were determined by sequence analysis of cDNA during reverse transcription. The 16S rRNA sequence of *Vibrio anguillarum* (Valle et al., 1990) was included in all analyses. This sequence has been corrected by the inclusion of a C-residue at position 418 (R. Wiik, pers. communication). Sequences, which are deposited under EMBL accession numbers as indicated in Table 1, consist of a continuous stretch varying in length between 1463 and 1481 nucleotides, corresponding to about 95.5% of the complete *E. coli* 16S rRNA sequence (Brosius et al. *Proc. Natal Acid. Sci. USA* 78:4801–4805, 1978).

For the determination of intergeneric relationships the sequences were aligned to the homologous sequences of 6 members of the gamma subclass of proteobacteria. The root was determined using a member of the beta subclass as a reference. Regions of alignment uncertainties (positions 76 through 111, 1008 through 1034 and 1446 through 1486, *E.*

*coli* nomenclature [Brosius et al., 19783]) were omitted from the analysis. The pair-wise distances obtained are listed in Table 2, upper right triangle.

Turning now to FIG. 1, all vibrios form a coherent cluster that is adjacent to two other members of the Core of gamma-3 organisms (as defined by Woese et al., *Syst. Appl. Microbiol.*, 6:25–33, 1985), i.e. *E. coli* and *P. vulgaris*. The barophilic isolates from the North Atlantic (Liesack et al., 1991), *Ruminobacter amylophilus* and *Pseudomonas aeruginosa*, the latter two species, considered to be peripheral representatives of the gamma-3 subclass, are more remotely related. The branching pattern is in accord with those derived from 16S rRNA cataloguing (Stackebrandt and bioese, "Evolutions in prokaryotes," p. 1–31 in Carlile et al. (ed.), Molecular and Cellular Aspects of Microbial Evolution, Cambridge University Press, Cambridge 1981; Woese et al., 1984) and 5S rRNA sequences (MacDonell et al. *Microbiol. Sci.* 3:172–179, 1986). As already discussed with 5S rRNA data (MacDonell et al, 1986) the phylogenetic depth of the Vibrio cluster is comparable to that of the Enterobacterlaceae cluster, considering that Escherichia and Proteus are the phylogenetically most diverse genera of this family (Brenner et al. "Enterobacteriaceae, Rahn 1937" page 408–420, in Krieg et al. (eds), Bergey's Manual of Systematic Bacteriology, Vol. 1, Williams & Wilkins Co., Baltimore, 1984; MacDonell et al., 1986).

The distinct separation of the vibrios from moderately related genera is also expressed by the occurrence of genus-specific signatures In the secondary structure of the 16S rRNA (Table 3). It has however been kept in mind that the data base of published 16S rRNA sequences of gamma-3 organisms is small and so called "specific" features may be blurred with additional sequences becoming available.

For determination of the intrageneric branching pattern the *E. coli* sequence served as an out-group reference. The pair-wise distances (Hamming) are Indicated in Table 2, lower left triangle. The overall similarity between the ten Vibrio sequences Is 85.6%. Seven species appear to be closely related, sharing an overall sequence similarity of 91.3%. Of these seven species, *V. alginolyttcus*, *V. camobellit*, *V. harveyi* and *V. natriegens*, as well as *V. parahaemolyticus* and *V. vulnificus* form even phylogenetically tighter groups, with *V. proteolyticus* branching off intermediate to these two groups. *Vibrio (Lisonelia) alginolyticus*, *V. diazotrophicus*, and *V. hollisae* represent individual sublines of descent, with the latter species representing the earliest branch within Vibrio.

The clustering of the core organisms of Vibrio correlates by and large with results of DNA reassociation experiments. Especially the grouping of *V. harveyi*, *V. campbellii* and *V. alginolyticus* is confirmed, as is the more isolated position of *V. vulnificus* and *V. proteolyticus* (Reichelt et al., *Arch. Microbiol.*, 110:101–120, 1976; see also Bauman et al., *Ann. Rev. Microbiol.*, 37:369–398 1983). The position of *V. parahaemolyticus* is not as clear-cut. While this species was shown to be highly related to *V. alginolyticus* (65% DNA similarity according to Reichelt et al., 1978)) it clusters with *V. vulnificus* by 16S rRNA similarities. In a more recent DNA/DNA hybridization study (Molitoris et al., *Int. J. Syst. Bacteriol.*, 39:442–449, 1989), however, *V. parahaemolyticus* and *V. alginolyttcus* were found to be less closely related, viz. around 45% and 22%. under optimal and stringent reassociation conditions, respectively. Immunological relationships of superoxide dismutases cluster all core organisms of Vibrio investigated by rRNA analysis, with the exception of *V. vulnificus* that grouped by its own (Bauman et al., 1983). Comparison of 16S and 5S rRNA branching patterns of Vibrio core organisms reveal more significant differences than found in the comparison of results from DNA pairing and 16S rRNA analysis. The topography of the 5S rRNA tree generated by MacDonell et al. (1986) sees only *V. parahaemolyticus*, *V. alginolytlcus*, *V. natriegens* and *V. proteolyticus* as well as *V. diazotroohicus* to form a tight cluster. Using the similarity values for principal component analysis the relationships change in that *V. dtazotroohius* is as unrelated to core species as are *V. harveyi* and *V. vulnificus*. In a more recent tree ((Colwell et al., "Polyphasic taxonomy of the genus Vibrio", abstr. 01–21, p. 134, *Abstr. Int. Union Microbiol. Sci. Congr.: Bacteriol. Mycol.*, Osaka, Japan, 1990), *V. harveyl* does cluster with core organisms (as in 16S rRNA analysis).

A consistent finding in molecular systematic studies is the lack of close relationship between *V. anguillarum* and the core organisms. Principal component analysis (MacDonell et al., 1986) and DNA reassoctation experiments revealed the isolated position of this species which lead to the description of a new genus Listonella to harbor *V. anguillarum* and related species, i.e. *V. damsel* and *L. pelagia* & (MacDonell and Colwell, Syst. appl. Microbiol. 1985). *V. hollisae*, however, described as a probable cause of human diarrhea (Hickman et al., *J. Clin. Microbiol.*, 15:395–401 1982) is even more remote, evolutionarily, from the core organisms than Is *V. anguillarum* as indicated by the lack of significant DNA similarities (Hickman et al., 1982) to other Vibrio species and by the results of this study. From a phylogenetic point of view, *V. hollisae* should be elevated to genus rank if the genus Listonella is accepted by taxonomists.

The position of *V. diazotrophtcus* in the 16S rRNA tree is a moot point. Using the Fitch and Margoliash *Science,* 155:279–284 (1967), (1968) algorithm on 5S rRNA similarity data this species appeared closely related to *V. proteolyticus* while, as mentioned above, it grouped outside the constraints of the Vibrio core organisms in principal component analysis (MacDonell et al., 1986). Low DNA similarity values (Guerinot et al. *J. Syst. Bacteriol.*, 36:350–557, 1982) and results of numerical phenetic analysis (West et al. *J. Syst. Bacterial.*, 36:531–543, 1986, 1986) confirmed the isolated position of *V. dizotrophtcus*. Support for the conclusion that this species does not belong to the core organisms is based on the analysis of the fatty acid composition. Urdaci et al. (1990) showed that Res. Microbiol 141:437–452 *V. diaotrophicus*, like *V. anquillarum*, *V. fischeri*, *V. gazogenes*, *V. damsela* and *V. ordalii* lack fatty acids of the 12:0-, 17:0- and 17:1 types, which are present, either alone or in combination with each other, in members of the core of Vibrio.

The needs for rapid diagnostic methods for water-, fish-, mussels- and oyster-born human pathogens (Blake et al. "Prevention of food-borne disease caused by Vibrio species", p. 579–591, in Colwell (ed.) Vibrios in the Environment, John Wiley & Sons, New York, 1984, Hood and Ness "The effects of storage on Vibrio concentrations in shellfish," p. 613–621Colwell (ed.) Vibrios in the Environment, John Wiley & Sons New York, 1984) make the variable 16S rRNA regions attractive targets for synthetic oligonucleotide probes and PCR primers.

Turning now to Table 3, it is anticipated that a region of the 16S ribosomal RNA has features unique to the genus Vibrio. The region extends from position 132 to 154. In particular, an area including nucleotides 137 through 141 (CUGAU), which area forms part of a helical structure with an area located between positions 222 through 226, may serve as a target for which complementary nucleic acid will preferentially hybridize over rRNA and rDNA of non-Vibrio bacteria. Such nucleic acid will comprise sequences 137 through 141 or their complement and such other nucleotides to allow such nucleic acid to exhibit stable preferential hybridization to such target area. Preferably, the nucleic acid includes sequences extending to positions 132 and 154 which positions are specific for Vibrio bacteria.

The first species-specific 16S rRNA-based probe for vibrios had been designed for *V. anguillarum* (Rehnstam et el. *Appl. Environ. Microbiol.*, 55:1907–1910, 1989) which targets a stretch between positions 431 and 455 (*E. coli* nomenclature). As compared to the homologous regions of other Vibrio species, the only difference is the presence of a U-residue at position 434 in the *V. anguillarum* sequence. All other Vibrio species possess a C-residue (transition from G-C to A-U at positions 408 and 434). Although the probe had not been tested against any of the species included in this study, the position of the altered nucleotide near the 3' terminus of the probe makes it highly likely that it fails to bind to rRNA of strains of other species.

Turning now to Table 4, three more highly variable regions are found between positions 73 through 100, 180 through 196 and 455 through 477. Although certain pairs have identical or highly similar sequences, these regions offer the potential to discriminate between each species investigated in this study. The differences appear to be sufficiently significant that their selectivity can be predicted (a single nucleotide difference within a 20-mer probe has been used to selectively detect streptomycetes [Witt et el., "Identification of streptomycetes by 16S rRNA sequences and oligonucleotide probes" p. 679–684, in Hattort et al (eds.), Recent Advances in Microbial Ecology, Japan Scientific Society Press, Tokyo, 1989] and *M. leprae* [Liesack et el., *Lett. Appl. Microbiol.*, 11:96–66, 1990 Stackebrandt et al. *Acta Leprol.*, 7:222–225, 1989] among closely related species). Interestingly, one of the most highly variable regions in the eubacterial 16S rRNA, i.e. around position 465 (*E. coli* nomenclature), exhibits the same sequence for *V. camobellii, V. aiginolyticus, V. harveyi* and *V. natriegens*.

The distances between the three variable regions of either 100, 180 or 280 nucleotides are large enough to apply PCR diagnosis (Boeddtnghaus et al. *J. Clin. Microbiol.*, 28:1751–1759, 1990) where either two of the regions serve as target sites for PCR primers. At least for certain strains the differences in the target regions are sufficiently large to encourage application of this modern identification tool. The ease with which DNA can be extracted from Gram-negative bacteria should facilitate rapid diagnosis of pathogenic Vibrio species directly in the environment.

In addition, the probes of the present invention can be used in combination in a sandwich assay. In a typical sandwich assay, a detector probe and a capture probe are brought in contact with a sample. The capture probe includes a ligand capable of binding to an antiligand on a support. A detector probe includes a label. At least one probe of the capture probe and detector probe is capable of preferentially hybridizing to the rRNA or rDNA of the Vibrio bacteria. The remaining probe may preferentially hybridize to rRNA or rDNA of Vibrio bacteria, or the remaining probe may be capable of binding to rRNA or rDNA of a larger number of organisms if at least one probe has the specificity desired.

The detector probe and capture probe are allowed to form a hybridization product in the presence of Vibrio rRNA or rDNA comprising a detector probe-capture probe-target complex. The detector probe and capture probe bind to substantially contiguous areas of the target. The complex is captured on a support, and the support washed of extraneous matter.

The support, or elutions from the support which include the detector probe as part of the complex, is monitored to detect the detector probe as an indication of the presence of the target.

The label may include any commonly applied means capable of detection. In addition, the probe sequences may be included in a nucleic acid capable of amplification. An example of such nucleic acid includes a MDV-1 sequences capable of replication by the enzyme Q-Beta repltcase.

Thus, the present invention provides compositions and methods for the detection of bacteria in the genus Vibrio. Individuals skilled in the art will readily recognize that the present invention is subject to modification and alteration which modifications and alterations should be considered within the purview of the present invention as set forth in the claims below.

TABLE 1

Vibrio species investigated and the EMBL accession numbers of their 16S rRNA.

| Species | Source | Accession number |
|---|---|---|
| V. anguillarum | NCMB 6 (=ATCC 19264, type) | 16895 |
| V. campbelli | ATCC 25920 (type) | X16895 |
| V. alginolyticus | ATCC 17749 (type) | X56576 |
| V. diazotrophicus | ATCC 33466 (type) | X56577 |
| V. harveyi | ATCC 14126 (type) | X56578 |
| V. proteolyticus | ATCC 15338 (type) | X56579 |
| V. parahemolyticus | ATCC 17802 (type) | X56580 |
| V. natriegens | ATCC 14048 (type) | X56581 |
| V. vulnificus | ATCC 27562 (type) | X56582 |
| V. hollisae | ATCC 33564 (type) | X56583 |

TABLE 2

Equally weighted (Hamming) distances[a] between 16S rRNA sequence pairs of Vibrio species and other members of the gamma subclass of Proteobacteria. *Ps. testosteroni* is an outgroup reference organisms (beta subclass of Proteobacteria)

| | Hamming distances | | | | | | | | | | | | | | | | |
|---|---|---|---|---|---|---|---|---|---|---|---|---|---|---|---|---|---|
| Organisms | 1 | 2 | 3 | 4 | 5 | 6 | 7 | 8 | 9 | 10 | 11 | 12 | 13 | 14 | 15 | 16 | 17 |
| 1. V. parahaemolyticus | 0 | 77 | 101 | 94 | 94 | 93 | 96 | 113 | 108 | 136 | 207 | 220 | 221 | 252 | 262 | 281 | 336 |
| 2. V. vulnificus | 51 | 0 | 105 | 91 | 94 | 93 | 95 | 109 | 110 | 137 | 203 | 213 | 216 | 243 | 256 | 279 | 333 |
| 3. V. proteolyticus | 61 | 66 | 0 | 94 | 97 | 94 | 99 | 119 | 123 | 135 | 196 | 212 | 214 | 247 | 266 | 282 | 348 |
| 4. V. natriegens | 64 | 65 | 53 | 0 | 71 | 68 | 71 | 103 | 104 | 135 | 201 | 215 | 217 | 249 | 246 | 271 | 334 |

TABLE 2-continued

Equally weighted (Hamming) distances[a] between 16S rRNA sequence pairs of Vibrio species and other members of the gamma subclass of Proteobacteria. *Ps. testosteroni* is an outgroup reference organisms (beta subclass of Proteobacteria)

| Organisms | Hamming distances | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| 5. *V. campbellii* | 64 | 68 | 56 | 43 | 0 | 66 | 73 | 105 | 105 | 133 | 200 | 216 | 215 | 247 | 254 | 270 | 334 |
| 6. *V. alginolyticus* | 63 | 67 | 53 | 40 | 38 | 0 | 70 | 103 | 102 | 131 | 198 | 214 | 213 | 246 | 251 | 268 | 332 |
| 7. *V. harveyi* | 66 | 69 | 59 | 43 | 35 | 42 | 0 | 106 | 106 | 133 | 203 | 218 | 213 | 243 | 255 | 267 | 330 |
| 8. *V. anguillarum* | 88 | 77 | 81 | 76 | 78 | 76 | 79 | 0 | 115 | 153 | 212 | 215 | 228 | 250 | 266 | 285 | 341 |
| 9. *V. diazotrophicus* | 84 | 82 | 88 | 78 | 79 | 76 | 80 | 85 | 0 | 144 | 197 | 218 | 220 | 248 | 254 | 277 | 334 |
| 10. *V. hollisae* | 111 | 107 | 107 | 109 | 107 | 105 | 107 | 124 | 115 | 0 | 207 | 228 | 216 | 252 | 284 | 301 | 356 |
| 11. *E. coli*[1] | 186 | 184 | 182 | 178 | 177 | 175 | 180 | 190 | 176 | 184 | 0 | 155 | 220 | 272 | 258 | 273 | 330 |
| 12. *P. vulgaris*[1] | | | | | | | | | | | | 0 | 226 | 266 | 272 | 296 | 338 |
| 13. Barophile 1[2] | | | | | | | | | | | | | 0 | 157 | 263 | 278 | 329 |
| 14. Barophile 2[3] | | | | | | | | | | | | | | 0 | 284 | 301 | 356 |
| 15. *R. anylophilus*[1] | | | | | | | | | | | | | | | 0 | 266 | 347 |
| 16. *Ps. aeruginosa*[1] | | | | | | | | | | | | | | | | 0 | 302 |
| 17. *Ps. testosteroni*[1] | | | | | | | | | | | | | | | | | 0 |

[a]Regions of alignment uncertancies (see text) are omitted prior to the analyses.

TABLE 3

Sequence signature distinguishing members of Vibrio from other gamma-3 Proteobacteria.

| Position | Composition in | |
|---|---|---|
| | Vibrios | *E. coli* |
| 132 | U | C |
| 154–167 | C-G | U-A |
| 446–488 | U-G | G-C |
| 580–761 | U-A | C-G |
| 614–626 | G-C | C-G |
| 896–903 | U-A | C-G |
| 1123–1149 | G-C | U-A |

TABLE 4

Variable 16S rRNA stretches that could be used as targets for oligonucleotide probing and PCR diagnostic

| Organism | Position 73–100 | Position 180–196 | Position 455–477 |
|---|---|---|---|
| *V. alginolyticus* | CGAGUUAACUGGAACUUGGGAACGAUAACGGCGUUG | AAUGCCUACGGGCCAA | UAGUGUAGUUAAUAGCUGCAUUA |
| *V. campbellii* | CGAGUUAACUGGAACUUGGGAACGAUAACGGCCUCG | AAUGCCUACGGGCCAA | UAGUGUAGUUAAUAGCUGCAUUA |
| *V. proteolyticus* | CGAGUUAUCUGAACUUCGGGAACGAUAUCGGCGUCG | AAUGCCUACGGGCCAA | UAGUGUAGUUAAUAGCUGCAUUA |
| *V. parahaemolyticus* | CGAGUUAUCUGAACUUCGGGAACGAUAACGGCGUCG | GAUAGCUUCGGGCUUAA | UGGCAGUGUUAAUAGCACUAUCA |
| *V. hollisae* | CGACAUGAACAAUCUUCGGGUGCGUUCAUGGGGCG | AAUAGCUUCGCGCUGAA | UAGCGUAGUUAAUACCUGCGUUA |
| *V. anguillarum* | CACAGAGGAACUUGUUCCUUGGGUGCG | GAUGCCUACGGGCCAA | UGGUGUUGUUAAUAGCAGACAUCA |
| *V. diazotrophicus* | CACAGAGAAACUUGUUUCUCGGGUGCG | AAUGUCUCGGACGAA | UGGUGUAGUUAAUAGCAGCAUCA |
| *V. vulnificus* | CACAGAGAAACUUGUUUCUCGGGUGGCG | GAUAGCUUCGGGCUUAA | UGGUAGUGUUAAUAGCACUAUCA |
| *V. harveyi* | CGAGUUAUCUGGAA . . .¹ | AAUACCUACGGGGUCAA | UAGUGUAGUUAAUAGCUGCAUUA |
| *V. natriegens* | CGAGUUAAC . . .¹ | GAUGCCUACGGGCCAA | UAGUGUAGUUAAUAGCUGCAUUA |

What is claimed is:

1. An isolated nucleic acid consisting of a nucleotide sequence which is identical or fully complementary to at least 10 consecutive nucleotides of any one of SEQ ID NOs: 1 to 5, 7, 8, 10 to 12, 14 to 20, 22, or 23, which nucleic acid preferentially hybridizes to the 16S rRNA or rDNA of *Vibrio alginolytius, Vibrio campbellii, Vibrio proteolyticus, Vibrio parahaemolyticus, Vibrio hollisae, Vibrio diazotrophicus, Vibrio vulnificus, Vibrio harveyi*, or *Vibrio natriegens* over the rRNA or rDNA of non-Vibrio bacteria.

2. A nucleic acid of claim 1, wherein said nucleotide sequence is identical or fully complementary to any one of SEQ ID NOs: 1 to 5, 7, 8, 10 to 12, 14 to 20, 22, or 23.

3. A probe comprising the nucleic acid of claim 2 and one or more agents wherein said agent is a label, a amplifying agent, or a detectable agent.

4. A probe of claim 3, wherein said amplifying agent is an MDV-1 sequence replaceable by Q-beta replicase.

5. A probe comprising the nucleic acid of claim 1 and one or more agents wherein said agent is a label, an amplifying agent, or a detectable agent.

6. A probe of claim 5, wherein said amplifying agent is an MDV-1 sequence replaceable by Q-beta replicase.

7. A method for detecting the presence of *Vibrio alginolyticus, Vibrio campbellii, Vibrio proteolyiicus, Vibrio parahaemolyticus, Vibrio hollisae, Vibrio diazotrophicus, Vibrio vulnificus, Vibrio harveyi*, or *Vibrio natriegens* bacteria in a sample comprising the steps of:

a) contacting said sample with at least one nucleic acid of claim 1 corresponding to said Vibrio species to be detected;

b) imposing hybridization conditions on the sample and said nucleic acid which allow said nucleic acid to hybridize to the rRNA or rDNA of said Vibrio bacteria, if present, to form nucleic acid complexes, said conditions not allowing said nucleic acid to form stable hybridized nucleic acid complexes with any non-Vibrio bacteria; and c) detecting said nucleic acid complexes as an indication of the presence of Vibrio bacteria in the sample.

8. An isolated nucleic acid of claim 1, wherein said nucleotide sequence is identical or fully complementary to SEQ ID NO: 1.

9. An isolated nucleic acid of claim 1, wherein said nucleotide sequence is identical or fully complementary to SEQ ID NO: 2.

10. An isolated nucleic acid of claim 1, wherein said nucleotide sequence is identical or fully complementary to SEQ ID NO: 3.

11. An isolated nucleic acid of claim 1, wherein said nucleotide sequence is identical or fully complementary to SEQ ID NO: 4.

12. An isolated nucleic acid of claim 1, wherein said nucleotide sequence is identical or fully complementary to SEQ ID NO: 5.

13. An isolated nucleic acid of claim 1, wherein said nucleotide sequence is identical or fully complementary to SEQ ID NO: 7.

14. An isolated nucleic acid of claim 1, wherein aid nucleotide sequence is identical or fully complementary to SEQ ID NO: 8.

15. An isolated nucleic acid of claim 1, wherein said nucleotide sequence is identical or fully complementary to SEQ ID NO: 10.

16. An isolated nucleic acid of claim 1, wherein said nucleotide sequence is identical or fully complementary to SEQ ID NO: 11.

17. An isolated nucleic acid of claim 1, wherein said nucleotide sequence is identical or fully complementary to SEQ ID NO: 12.

18. An isolated nucleic acid of claim 1, wherein said nucleotide sequence is identical or fully complementary to SEQ ID NO: 14.

19. An isolated nucleic acid of claim 1, wherein said nucleotide sequence is identical or fully complementary to SEQ ID NO: 15.

20. An isolated nucleic acid of claim 1, wherein said nucleotide sequence is identical or fully complementary to SEQ ID NO: 16.

21. An isolated nucleic acid of claim 1, wherein said nucleotide sequence is identical or fully complementary to SEQ ID NO: 17.

22. An isolated nucleic acid of claim 1, wherein said nucleotide sequence is identical or fully complementary to SEQ ID NO: 18.

23. An isolated nucleic acid of claim 1, wherein said nucleotide sequence is identical or fully complementary to SEQ ID NO: 19.

24. An isolated nucleic acid of claim 1, wherein said nucleotide sequence is identical or fully complementary to SEQ ID NO: 20.

25. An isolated nucleic acid of claim 1, wherein said nucleotide sequence is identical or fully complementary to SEQ ID NO: 22.

26. An isolated nucleic acid of claim 1, wherein said nucleotide sequence is identical or fully complementary to SEQ ID NO: 23.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:1:

CGAGUUAACU GGAACUUGGG AACGAUAACG GCGUUG 36

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:2:

CGAGUUAACU GGAACUUGGG AACGAUAACG GCGUCG 36

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

CGAGUUAUCU GAACUUCGGG GAACGAUAUC GGCGUCG 37

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:4:

CGAGUUAUCU GAACUUCGGG GAACGAUAAC GGCGUCG 37

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:5:

CGACAUGAAC AAUCUUCGGG UGCGUUCAUG GGCGGCG    37

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:6:

CACAGAGGAA CUUGUUCCUU GGGUGGCG    28

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:7:

CACAGAGAAA CUUGUUUCUC GGGUGGCG    28

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:8:

CGAGUUAUCU GGAA    14

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:9:

CGAGUUAAC    9

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:10:

AAUGCCUACG GGCCAA    16

(2) INFORMATION FOR SEQ ID NO:11:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:11:

GAUAGCUUCG GCUUAA      16

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:12:

AAUAGCUUCG GCUGAA      16

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:13:

GAUGCCUACG GGCCAA      16

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:14:

AAUGUCUUCG GACGAA      16

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:15:

GAUAGCUUCG GCUUAA      16

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (ii) MOLECULE TYPE: RNA (xi) SEQUENCE DESCRIPTION: SEQ ID NO:16:

AAUACCUACG GGUCAA                                                              16

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:17:

GAUGCCUACG GGCCAA                                                              16

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:18:

UAGUGUAGUU AAUAGCUGCA UUA                                                      23

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:19:

UGGCAGUGUU AAUAGCACUA UCA                                                      23

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:20:

UAGCGUAGUU AAUACCUGCG UUA                                                      23

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:21:

UGGUGUUGUU AAUAGCAGCA UCA                                                              23

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:22:

UGGUAGUGUU AAUAGCACUA UCA                                                              23

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:23:

UAGUGUAGUU AAUAGCUGCA UUA                                                              23